United States Patent
Wang

(10) Patent No.: US 9,562,699 B2
(45) Date of Patent: Feb. 7, 2017

(54) AIR CONDITIONER

(71) Applicant: Hsiu-Fen Wang, Tainan (TW)

(72) Inventor: Hsiu-Fen Wang, Tainan (TW)

( * ) Notice: Subject to any disclaimer, the term of this patent is extended or adjusted under 35 U.S.C. 154(b) by 122 days.

(21) Appl. No.: 14/731,583

(22) Filed: Jun. 5, 2015

(65) Prior Publication Data

US 2016/0356510 A1 Dec. 8, 2016

(51) Int. Cl.
| | |
|---|---|
| *B01D 53/02* | (2006.01) |
| *F24F 3/14* | (2006.01) |
| *B01D 53/04* | (2006.01) |
| *B01D 53/26* | (2006.01) |
| *A61L 9/00* | (2006.01) |

(52) U.S. Cl.
CPC .............. *F24F 3/1411* (2013.01); *A61L 9/00* (2013.01); *B01D 53/02* (2013.01); *B01D 53/04* (2013.01); *B01D 53/261* (2013.01); *B01D 2253/102* (2013.01); *B01D 2257/90* (2013.01)

(58) Field of Classification Search
CPC ........ F24F 3/1411; B01D 53/02; B01D 53/04; B01D 53/26; B01D 53/261; B01D 2253/102; B01D 2257/90; B01D 2259/40088; A61L 9/00
USPC .... 95/118, 119, 143, 146, 147; 55/512, 515, 55/516, 519; 422/120
See application file for complete search history.

(56) References Cited

U.S. PATENT DOCUMENTS

| | | | | |
|---|---|---|---|---|
| 2,294,183 | A * | 8/1942 | Holm-Hansen | F24F 3/16 210/196 |
| 4,604,110 | A * | 8/1986 | Frazier | A61L 9/00 422/122 |
| 5,288,306 | A * | 2/1994 | Aibe | B01D 53/02 95/141 |
| 6,913,733 | B2 * | 7/2005 | Hardy | A61L 9/014 422/124 |
| 8,048,379 | B2 * | 11/2011 | Sassoon | A01M 1/2033 206/485 |
| 8,679,215 | B2 * | 3/2014 | Lim | B01D 53/0415 55/470 |
| 2003/0012680 | A1 * | 1/2003 | Balsys | A61L 9/042 422/5 |
| 2003/0175171 | A1 * | 9/2003 | Yamamoto | A01M 1/2033 422/124 |

* cited by examiner

*Primary Examiner* — Frank Lawrence
(74) *Attorney, Agent, or Firm* — Rosenberg, Klein & Lee

(57) ABSTRACT

An air conditioner having an absorption unit with a box and a fan unit is revealed. The box is disposed with a ventilation unit and loaded with absorbing material used as desiccant/ deodorant. An exhaust hole of the fan unit is communicated with the ventilation unit of the absorption unit. For removing moisture or odors, air outside is drawn by the fan unit and blown into the absorption unit by the ventilation unit. After moisture or pollutants being absorbed by the absorbing material, the air is exhausted by through holes of the box. The fan unit is switched to a heating mode when the absorbing material is saturated with moisture or pollutants. Then air outside is heated by an electric heating unit of the fan unit and is delivered to the absorption unit for drying the absorbing material or baking out the pollutants. Thus the absorbing material is reactivated.

7 Claims, 4 Drawing Sheets

AIR CONDITIONER

BACKGROUND OF THE INVENTION

Field of the invention

The present invention relates to an air conditioner, especially to an air conditioner that is having simple structure, with low cost, with low power consumption, not easily damaged, space saving, and environmental protective.

Descriptions of Related Art

Generally the air conditioner available now includes a machine body disposed with components such as a fan motor, a condenser, an evaporator, a compressor, etc. While in use, moisture indoors is drawn into the machine body by the fan motor. Then the air is passed through the condenser and evaporator for heat transfer and the moisture in the air becomes liquid water. The liquid water is collected by a storage box. Thereby the air exhausted from the air conditioner is with reduced moisture. However, the air conditioner formed by the above components, such as the fan motor, the condenser, the evaporator, the compressor etc. is having high cost, with high power consumption, with large volume that is difficult to be disposed and stored, easily damaged and having increased high maintenance cost. Moreover, coolants required for heat removal deplete stratospheric ozone. Thus the coolants are not environmental friendly. The air conditioner available now also doesn't provide the function of odor/pollutant removal.

SUMMARY OF THE INVENTION

Therefore it is a primary object of the present invention to provide an air conditioner that is having simple structure, with low cost, with low power consumption, not easily damaged, space saving, and environmental protective.

In order to achieve the above objects, an air conditioner of the present invention includes an absorption unit and a fan unit. A receiving space of a box of the absorption unit is arranged with a ventilation unit. Bothe the box and the ventilation unit are disposed with a plurality of through holes. The receiving space of the box is loaded with several kinds of absorbing materials used as desiccants or deodorants. The fan unit is arranged adjacent to the absorption unit. An exhaust hole of the fan unit is communicated with a ventilation space of the ventilation unit of the absorption unit. While users intend to remove moisture or bad odors, air outside is drawn by the fan unit and is blown into the absorption unit by the ventilation unit. Then the air is exhausted by through holes of the box after moisture or pollutants in the air being absorbed by the absorbing materials. Moreover, the fan unit is switched to a heating mode when the absorbing materials are saturated with moisture or pollutants. Air outside is drawn by the fan unit and then is heated by an electric heating unit of the fan unit. Next the hot air is delivered to the absorption unit for heating and drying the absorbing materials or removal of the pollutants on the absorbing materials. Thus the absorbing material is reactivated and able to be reused.

BRIEF DESCRIPTION OF THE DRAWINGS

The structure and the technical means adopted by the present invention to achieve the above and other objects can be best understood by referring to the following detailed description of the preferred embodiments and the accompanying drawings, wherein.

DETAILED DESCRIPTION OF THE PREFERRED EMBODIMENT

Figure 1:
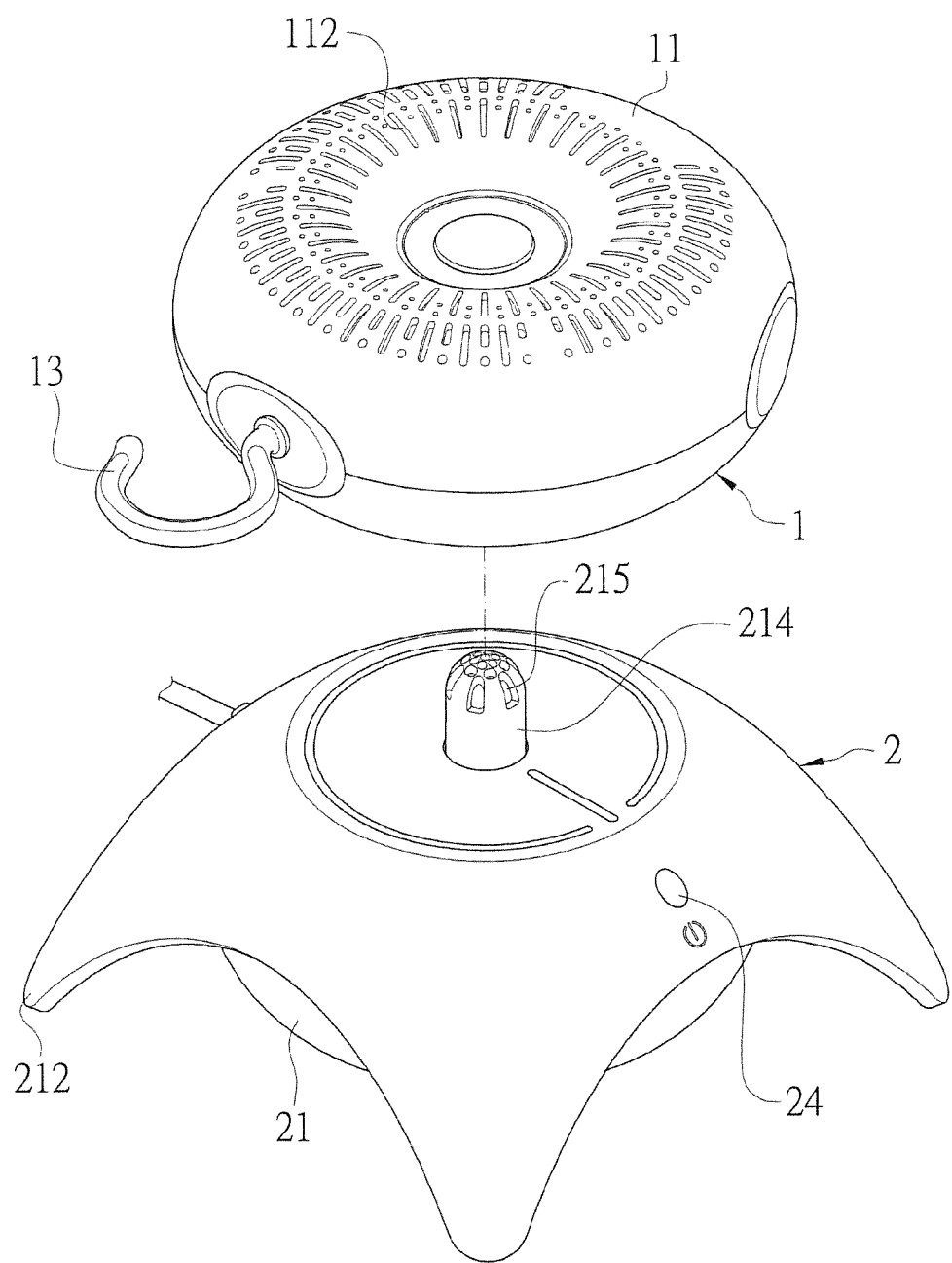
FIG. 1 is an explosive view of an embodiment according to the present invention.

Refer to FIG. 1, an air conditioner of the present invention includes an absorption unit 1 and a fan unit 2.

Figure 4:
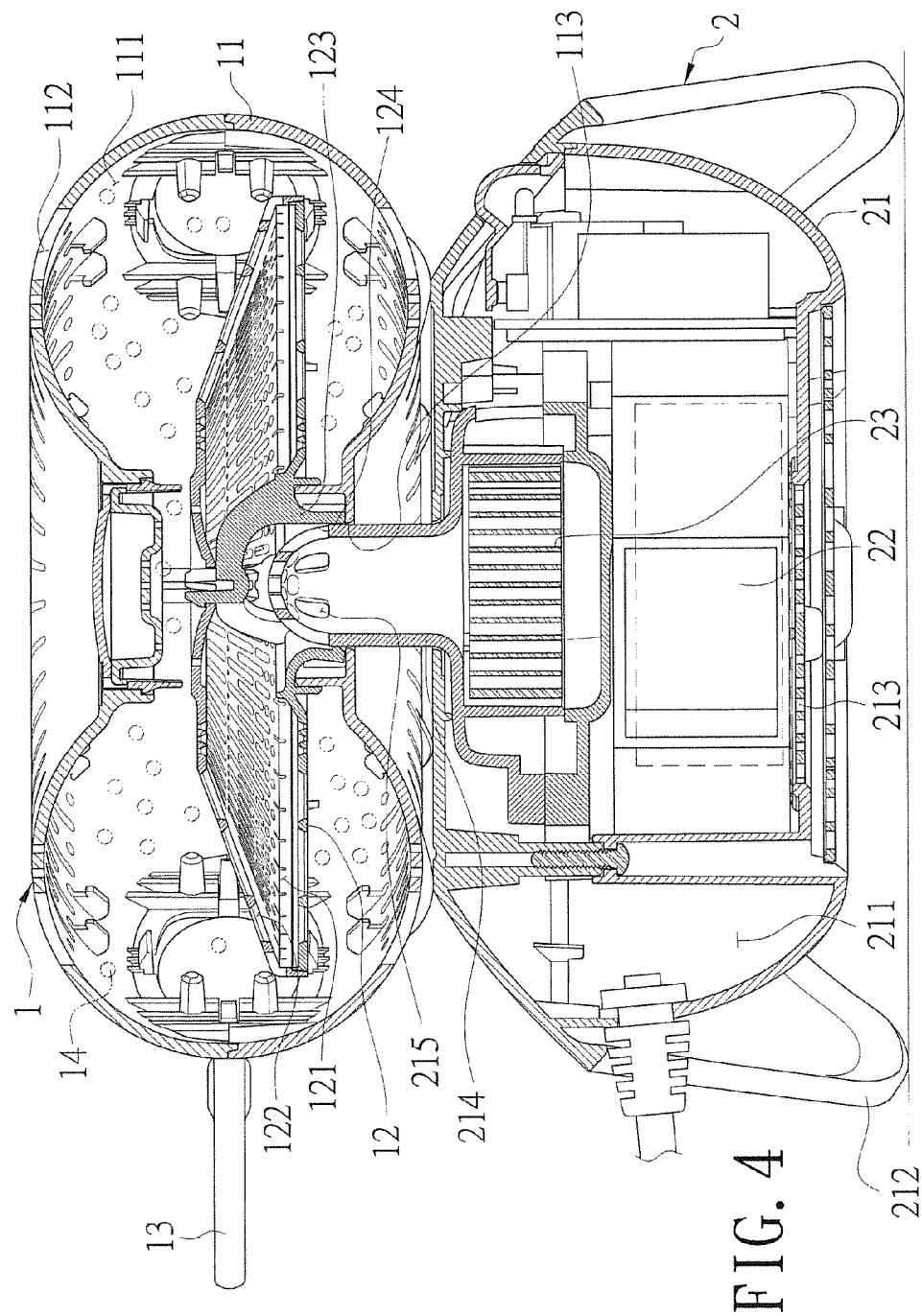
FIG. 4 is a longitudinal section of an embodiment according to the present invention.

Refer to FIG. 1 and FIG. 4, the absorption unit 1 includes a torus box 11 with a receiving space 111 therein. The box 11 is disposed with a plurality of through holes 112 communicating with the receiving space 111. An insertion hole 113 is arranged at a center of a bottom surface of the box 11. A ventilation unit 12 that is shaped like a truncated cone is mounted in the receiving space 111 and having a ventilation space 121. A plurality of through holes 122 is set on a top surface and a bottom surface of the ventilation unit 12 and communicating with the ventilation space 121. The ventilation space 121 of the ventilation unit 12 is communicated with the receiving space 111 of the box 11 by the through holes 122 thereof. A pipe 123 is connected to a center of a bottom surface with the largest diameter of the truncated conical ventilation unit 12. A pipe hole 124 of the pipe 123 is communicated with the ventilation space 121 while the pipe 123 of the ventilation unit 12 is communicated with the insertion hole 113 of the box 11. Thus the insertion hole 113 of the box 11 is communicated with the pipe hole 124 of the pipe 123 of the ventilation unit 12. Moreover, a hook 13 is set on a sidewall of the box 11. The receiving space 111 of the box 11 is used to load granules of at least one absorbing material 14. The absorbing material 14 can be silica gel desiccant or a deodorant made from a porous material such as activated carbon.

Figure 2:
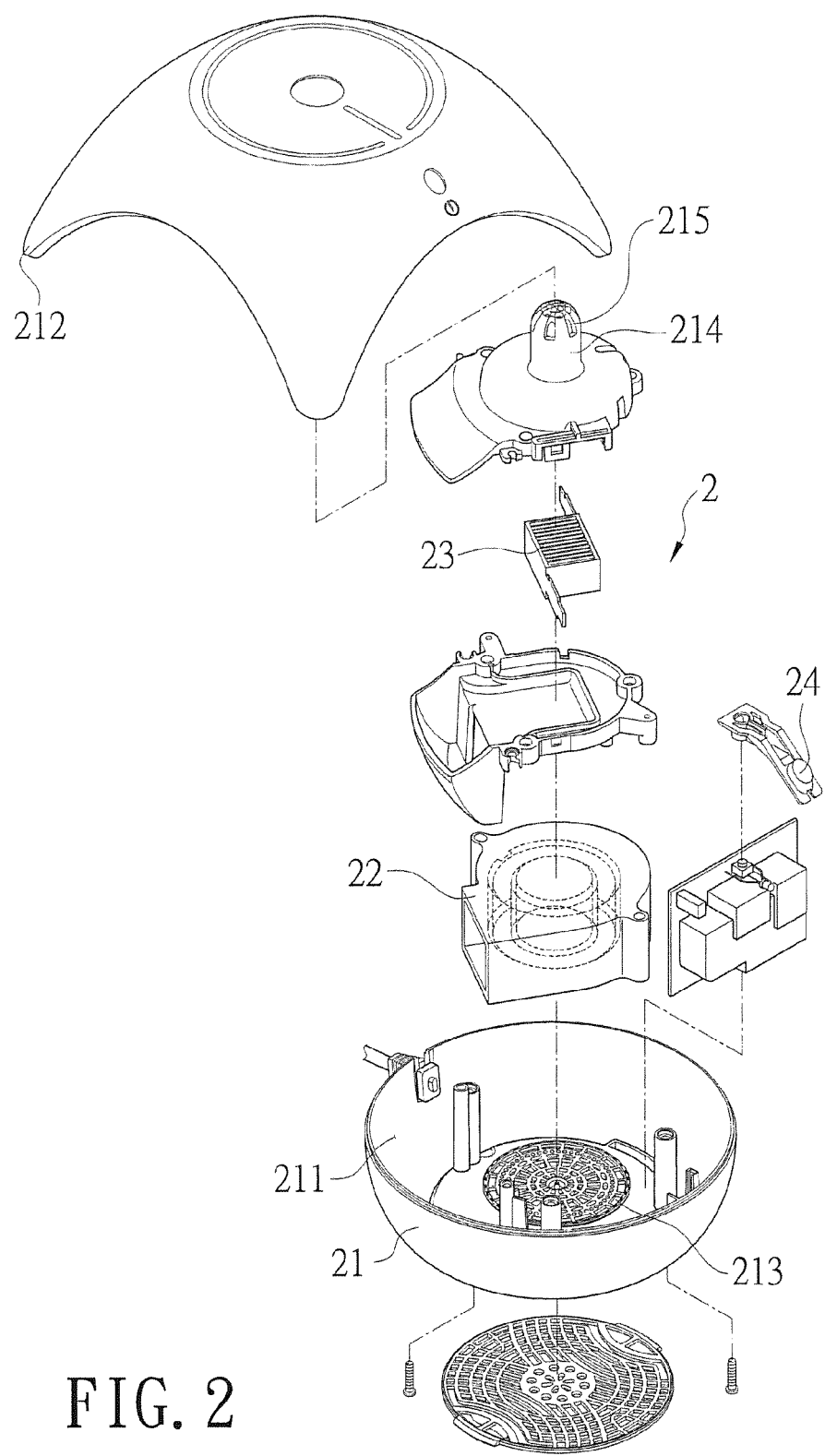
FIG. 2 is an explosive view of a fan unit of an embodiment according to the present invention.
Figure 3:
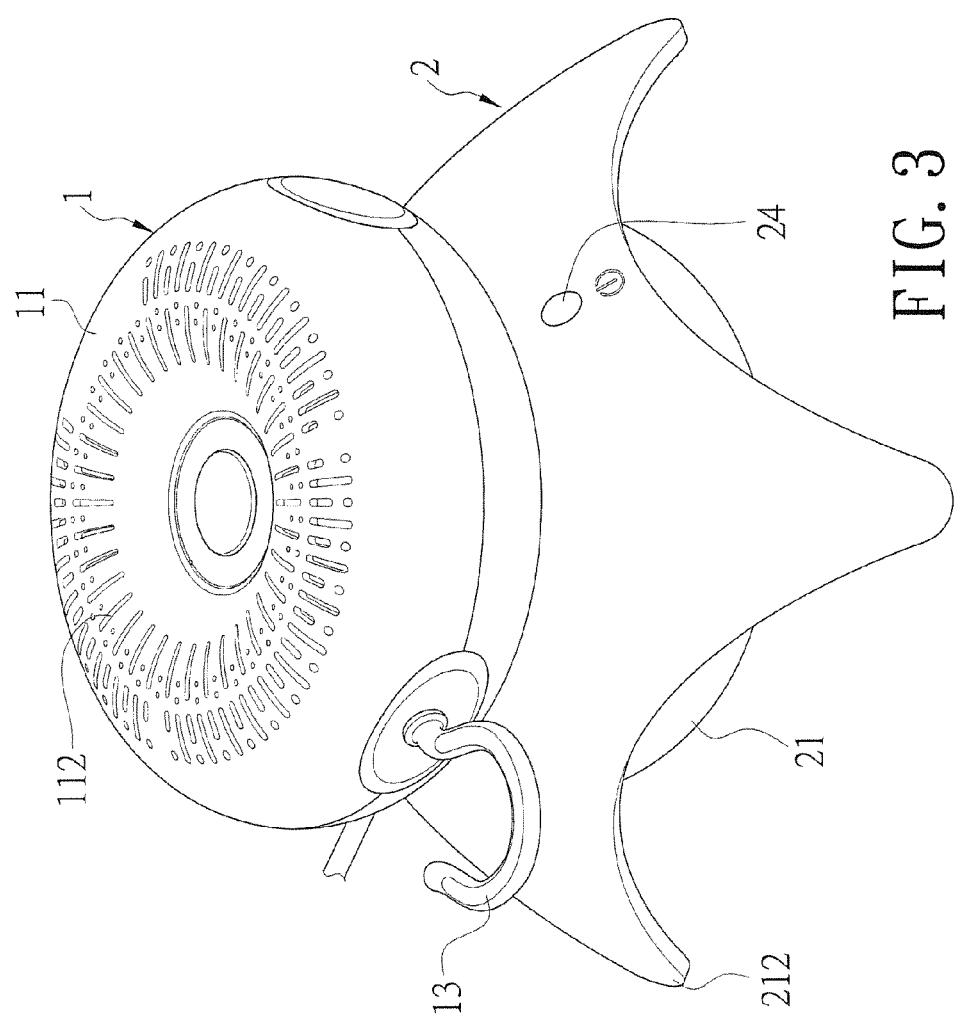
FIG. 3 is a perspective view of an embodiment according to the present invention.

Refer to FIG. 1 and FIG. 2, the fan unit 2 is moveably connected to the absorption unit 1 and having a loading seat 21, a blower unit 22, an electric heating unit 23 and a switch 24. A hollow portion 211 is formed in the loading seat 21 and a raised portion 212 extended from the loading seat 21 and used for supporting the bottom surface of the loading seat 21. Thus the bottom surface of the loading seat 21 is off the ground. A plurality of intake holes 213 is penetrating the bottom surface of the loading seat 21 and is communicated with the hollow portion 211 of the loading seat 21. The blower unit 22 is mounted in the hollow portion 211 of the loading seat 21 while the electric heating unit 23 is arranged over the blower unit 22. An exhaust pipe 214 is projecting from a center of a top end of the loading seat 21 and is mounted with at least one exhaust hole 215 for being communicated with the hollow portion 211. Moreover, the exhaust pipe 214 of the loading seat 21 is communicated with the insertion hole 113 of the absorption unit 1. The exhaust pipe 214 is passed through the pipe hole 124 of the pipe 123 of the ventilation unit 12 so that the exhaust hole 215 of the loading seat 21 is communicated with the pipe hole 124 of the ventilation unit 12 of the absorption unit 1. The switch 24 arranged at the loading seat 21 is connected to the blower unit 22 and the electric heating unit 23 and is used for control of a fan mode and a heating mode. The switch 24 is also connected to a power supply unit such as a power cord, etc.

When users intend to regulate moisture indoors, first take the absorption unit 1 with the absorbing material 14 and connect the absorption unit 1 to the fan unit 2. Then the switch 24 is switched to the fan mode. Now the switch 24 controls electric conduction to the blower unit 22 to make the blower unit 22 work. Next the blower unit 22 draws air outside into the hollow portion 211 of the loading seat 21 through the intake holes 213 on the bottom surface of the loading seat 21 and blows the air toward the exhaust pipe 214 on the top end of the loading seat 21. The air is flowed to the pipe hole 124 of the ventilation unit 12 of the absorption unit 1 through the exhaust hole 215 of the exhaust pipe 214. Then the air is passed through the pipe hole 124 of the ventilation unit 12, the ventilation space 121, and the through holes 122 on top and bottom surfaces of the ventilation unit 12, to the receiving space 111 of the box 11. At last, the air is passed through the desiccant/absorbing material 14 mounted in the receiving space 111 of the box 11 and moisture in the air is absorbed by the desiccant/absorbing material 14. Thereby the air exhausted through the through holes 112 of the box 11 is with reduced moisture.

When the absorbing material 14 in the absorption unit 1 is saturated with the moisture, the switch 24 of the fan unit 2 is switched to the heating mode. The switch 24 controls electrical conduction to the blower unit 22 and the electric heating unit 23 so as to make the blower unit 22 and the electric heating unit 23 work. At the moment, the switch 24 draws air in the hollow portion 211 of the loading seat 21 through the intake holes 213 on the bottom surface of the loading seat 21. The air is passed through the electric heating unit 23 and is heated by the electric heating unit 23. The heated air is blown to the exhaust pipe 214 on the top end of the loading seat 21 by the blower unit 22. Then the heated air is passed through the exhaust hole 215 of the exhaust pipe 214, the pipe hole 124 of the ventilation unit 12, and into the ventilation space 121. At last the heated air is blown into the receiving space 111 of the box 11 through the through holes 122 on top and bottom surfaces of the ventilation unit 12 so as to heat and dry the absorbing material 14 evenly. The absorbing material 14 is reactivated and recycled for moisture absorption.

Moreover, when users want to remove bad smells or pollutants such as bacteria etc in indoor air, they can take the absorption unit 1 and fill the deodorant formed by activated carbon. Then the absorption unit 1 is assembled with the fan unit 2. The fan unit 2 is switched to the fan mode by the switch 24. Similarly, the air outside is drawn into the loading seat 21 by the blower unit 22, then passed through the exhaust pipe 214 of the loading seat 21 to the absorption unit 1. Then odor absorbing material made from activated carbon in the receiving space 111 of the box 11 absorbs the odors and pollutants such as bacteria in the air. Thus the air exhausted through the through holes 112 of the box 11 of the absorption unit 1 and is clean without any weird odors.

While the absorbing material in the absorption unit 1 is saturated with pollutants, the switch 24 of the fan unit 2 is switched to the heating mode by users. Similarly, the air outside is introduced into the loading seat 21 by the blower unit 22 and then is heated by the electric heating unit 23.

The heated air is blown into the absorption unit 1 through the exhaust pipe 214 of the loading seat 21. The odor absorbing material made from activated carbon 14 in the receiving space 111 of the box 11 is heated. Thus the pollutants on the absorbing material 14 are baked out and the absorbing material 14 is reactivated. Therefore the absorbing material 14 is able to be reused for absorbing pollutants repetitively.

In summary, the air condition of the present invention has simple structure. Thus not only moisture or pollutants in the air is effectively removed, the manufacturing cost of the air conditioner is also significantly reduced. Moreover, the power consumption of the air conditioner is lowered, the damage rate is lowered and the maintenance cost is reduced. With proper volume, the air condition is space saving while in use. Once the air conditioner is used in places without power such as cabinets or closets for moisture absorption or odor elimination, the absorption unit 1 and the fan unit 2 of the present invention can be separated from each other. Then moisture absorption or odor elimination can still be achieved by absorbing capacity of the absorbing material 14 filled in the absorption unit 1 under the condition without power supply. By the hook 13 of the box, the absorption unit 1 is hung in closets, bookcases, shoe cabinets, storage cabinets etc. for moisture and odor absorption. As to the fan unit, it can be used to dry off clothes, shoes, etc. Thus the object of the present invention has multiple functions. In addition, the present invention uses the absorbing material 14 in the absorption unit 1 to absorb the moisture in the air, without the use of coolants. The absorbing material 14 can be reactivated and reused. The environmental protection effect is obvious.

What is claimed is:

1. An air conditioner comprising:
   an absorption unit having a box and a ventilation unit; the box including a receiving space formed therein, and a plurality of through holes disposed thereof and communicated with the receiving space; the ventilation unit arranged with a plurality of through holes, mounted in the receiving space and having a ventilation space therein; the ventilation space of the ventilation unit communicated with the receiving space of the box by the through holes thereof; the receiving space of the box loaded with a plurality of absorbing materials;
   a fan unit disposed adjacent to the absorption unit and having a loading seat with a hollow portion therein; at least one intake hole arranged at the loading seat and communicated with the hollow portion of the loading seat; a blower unit and an electric heating unit mounted in the hollow portion of the loading seat; an exhaust hole formed on the loading seat and communicated with the hollow portion; the exhaust hole of the fan unit communicated with the ventilation space of the ventilation unit of the absorption unit;
   wherein the exhaust hole of the fan unit is coupled to the ventilation unit of the absorption unit so that the absorption unit is assembled with the fan unit for absorption; or the absorption unit is separated from the fan unit and used for absorption independently.

2. The air conditioner as claimed in claim 1, wherein a switch is arranged at the loading seat of the fan unit and is coupled to the blower unit and the electric heating unit; the switch is used for control of a fan mode and a heating mode.

3. The air conditioner as claimed in claim 1, wherein a hook is set on a sidewall of the box of the absorption unit.

4. The air conditioner as claimed in claim 1, wherein the absorbing material is at least one desiccant.

5. The air conditioner as claimed in claim 1, wherein the absorbing material is a silica gel.

6. The air conditioner as claimed in claim 1, wherein the absorbing material is at least one deodorant.

7. The air conditioner as claimed in claim 1, wherein the absorbing material is activated carbon.

* * * * *